(12) United States Patent
Chen et al.

(10) Patent No.: US 7,335,722 B2
(45) Date of Patent: Feb. 26, 2008

(54) PEPTIDES USED AS ANGIOTENSIN CONVERTING ENZYME INHIBITOR AND PREPARATION PROCESS THEREOF

(75) Inventors: Yi-Hong Chen, Hsinchu (TW); Yung-Hsiang Yang, Hsinchu (TW); Yu-Hui Liu, Hsinchu (TW); Chien-Ti Chang, Hsinchu (TW); Hsiao-Hui Feng, Hsinchu (TW); Chu-Chin Chen, Hsinchu (TW)

(73) Assignee: Food Industry Research and Development Institute, Taipei (TW)

( * ) Notice: Subject to any disclaimer, the term of this patent is extended or adjusted under 35 U.S.C. 154(b) by 400 days.

(21) Appl. No.: 10/818,999

(22) Filed: Apr. 5, 2004

(65) Prior Publication Data

US 2004/0162244 A1    Aug. 19, 2004

Related U.S. Application Data

(62) Division of application No. 09/572,531, filed on May 17, 2000, now Pat. No. 6,767,990.

(30) Foreign Application Priority Data

Dec. 1, 1999    (CN)    ............................... 88 1 20997

(51) Int. Cl.
  *A61K 38/00*    (2006.01)
  *A61K 38/04*    (2006.01)
  *A61K 38/06*    (2006.01)
  *A23J 1/00*    (2006.01)
  *C12N 9/00*    (2006.01)

(52) U.S. Cl. ...................... 530/300; 530/316; 530/330; 530/331; 530/412; 530/414; 435/183; 435/195; 435/219

(58) Field of Classification Search ................ 530/412, 530/414, 300, 316, 330, 331; 435/195, 219, 435/183
See application file for complete search history.

(56) References Cited

U.S. PATENT DOCUMENTS 5,314,807 A * 5/1994 Yoshikawa et al. ........ 435/68.1

FOREIGN PATENT DOCUMENTS

JP    08231588 A  *  9/1996

* cited by examiner

*Primary Examiner*—Jon Weber
*Assistant Examiner*—Rita Mitra

(57) ABSTRACT

The invention discloses five peptides which can be used as angiotensin converting enzyme inhibitor. The subject invention also discloses a process for the preparation of the products having angiotensin converting enzyme inhibitory activity, which comprises the following steps: (a) adding protein hydrolase to the solution of chicken residues for reaction; (b) separating the chicken residues and liquid after the reaction of step (a) and collecting the separated liquid; and (c) drying the liquid obtained from step (b) to obtain the products.

1 Claim, 6 Drawing Sheets

PEPTIDES USED AS ANGIOTENSIN CONVERTING ENZYME INHIBITOR AND PREPARATION PROCESS THEREOF

CROSS REFERENCE TO RELATED APPLICATIONS

This is a divisional application of application Ser. No. 09/572,531, filed May 17, 2000 now U.S. Pat. No. 6,797,990.

BACKGROUND OF THE INVENTION

Angiotensin converting enzyme (ACE) mainly presents in human vascular endothelial cells, lungs, kidneys and brains. This enzyme may convert inactive angiotensin I to active angiotensin II by cleaving two amino acids (His-Leu) from the C-terminus end so as to cause contraction of blood vessels and increase blood pressure. Meanwhile, ACE may inactivate the bradykinin that exhibits the function of relief of blood vessels. Thus, ACE may increase blood pressure.

The binding of Angiotensin converting enzyme inhibitor (ACEI) to ACE may reduce the formation of angiotensin II and the inactivation of bradykinin. If ACEI is added to foods, it will cause positive effect on decreasing hypertensive symptom. For the present, it is known that many peptides have the effect on the inhibition of ACE. They have different amino acid sequences and lengths. Those peptides having ACE inhibitory activity can be isolated from foods. Those foods include the hydrolysates of animal or plant proteins, such as casein (Maruyama and Suzuki, 1982), corn protein (Miyoshi et al., 1991), sardine meat (Matsui et al., 1993) and bonito (Matsumura et al., 1993); and fermented foods, such as sake and wine residue (Saito et al., 1994), soy bean oil (Kinoshita et al., 1993), cheese (Okamoto et al., 1995) and fermented milk (Nakamura et al., 1995) etc.

Japanese Patent No. 5-87052 and Japanese Laid-Open Patent Publication No. 2-154693 disclose the substances containing oligopeptides. Food Chemical Monthly, 1990, 6:80 also discloses specific oligopeptides which have the improved effect on lipid metabolism, including the reduction of the concentration of triglyceride in blood. These substances containing oligopeptides described in the above patents or references are the mixtures of protein hydrolysates. However, they do no describe the amino acid sequences of the active ingredients of mixtures. The purity of the above-mentioned substances containing peptides is relatively low and can not be used as pharmaceuticals. Further, when those substances are contained in foods, they are very difficult to be quantitatively detected from other peptides contained in foods. This would cause some problems in quality control.

Japanese Laid-Open Patent Publication No. 6-298794 discloses a process for the preparation of ACEI from the proteins of animal and plant sources, such as fish meats, pork and chicken. The process utilizes protein hydrolase, such as thermolysin, pepsin or trypsin, in suitable medium and under proper conditions to decompose the starting materials. The hydrolysate is subject to centrifugation, filtration, concentration and resin absorption to obtain the peptides with ACE inhibitory activity. Japanese Laid-Open Patent Publication No. 5-331192 discloses the hydrolysis of katsubushi by thermolysin to produce the peptides with ACE inhibitory activity. The sequence of the peptide is H-Tyr-Ser-Trp-Ala-OH. Japanese Laid-Open Patent Publication No. 4-264098 discloses the preparation of the peptides with ACE inhibitory activity from chicken meats containing no fat. The sequence of the peptide is Gln-Lyn-Pro-Lys-Arg. U.S. Pat. No. 5,854,029 discloses a process for the preparation of the dipeptide Tyr-Pro exhibiting ACE inhibitory activity. In the process, lactobacillus is incubated in the peptide and/or protein medium containing Tyr-Pro to obtain an incubation solution containing a large amount of Tyr-Pro.

Among the above-mentioned prior art techniques, most of them utilize different hydrolase, separation and purification method from animal proteins, such as fish meat, chicken or pork to prepare the peptides with ACE inhibitory activity. However, the cost of the starting materials is more expensive.

SUMMARY OF THE INVENTION

The Applicant found that hydrolysis of the wastes produced from the manufacture of chicken essence and further treatment of the waste mixture with hydrolase may obtain the products having strong ACE inhibitory activity. The process is of low cost and may improve the values of chicken essence by-products.

The main object of the invention is to provide novel peptides having ACE inhibitory activity.

Another object of the invention is to provide a process for the preparation of the products having ACE inhibitory activity. The process comprises the treatment of chicken residues with protein hydrolase to obtain the products having ACE inhibitory activity. The products can be used in health foods.

BRIEF DESCRIPTIN OF THE DRAWINGS

Figure 4:
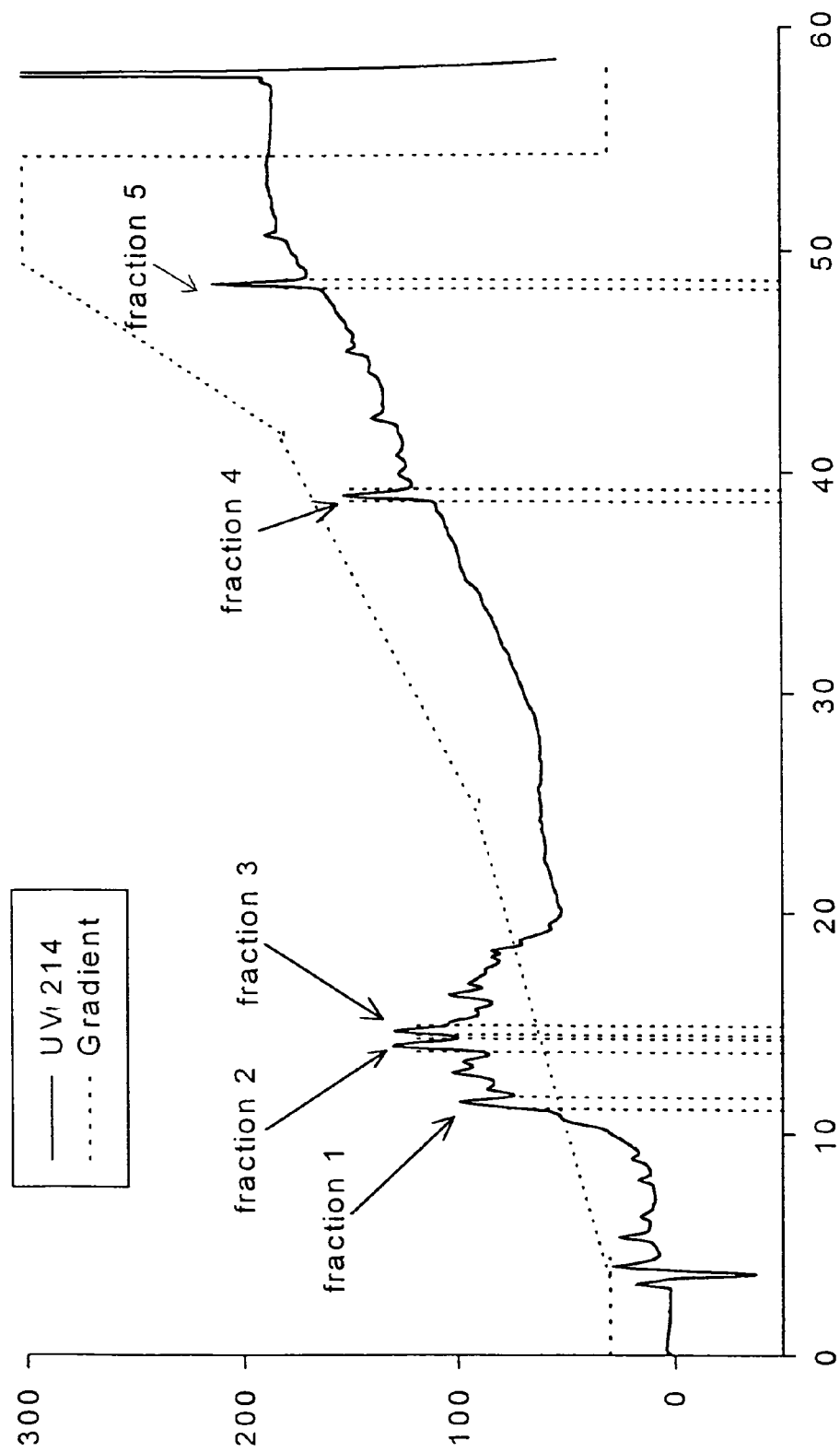

FIG. 4 also shows the result of purification of the peptides prepared according to the invention at the fourth stage by use of an analytical class C-18 column.

Figure 5:
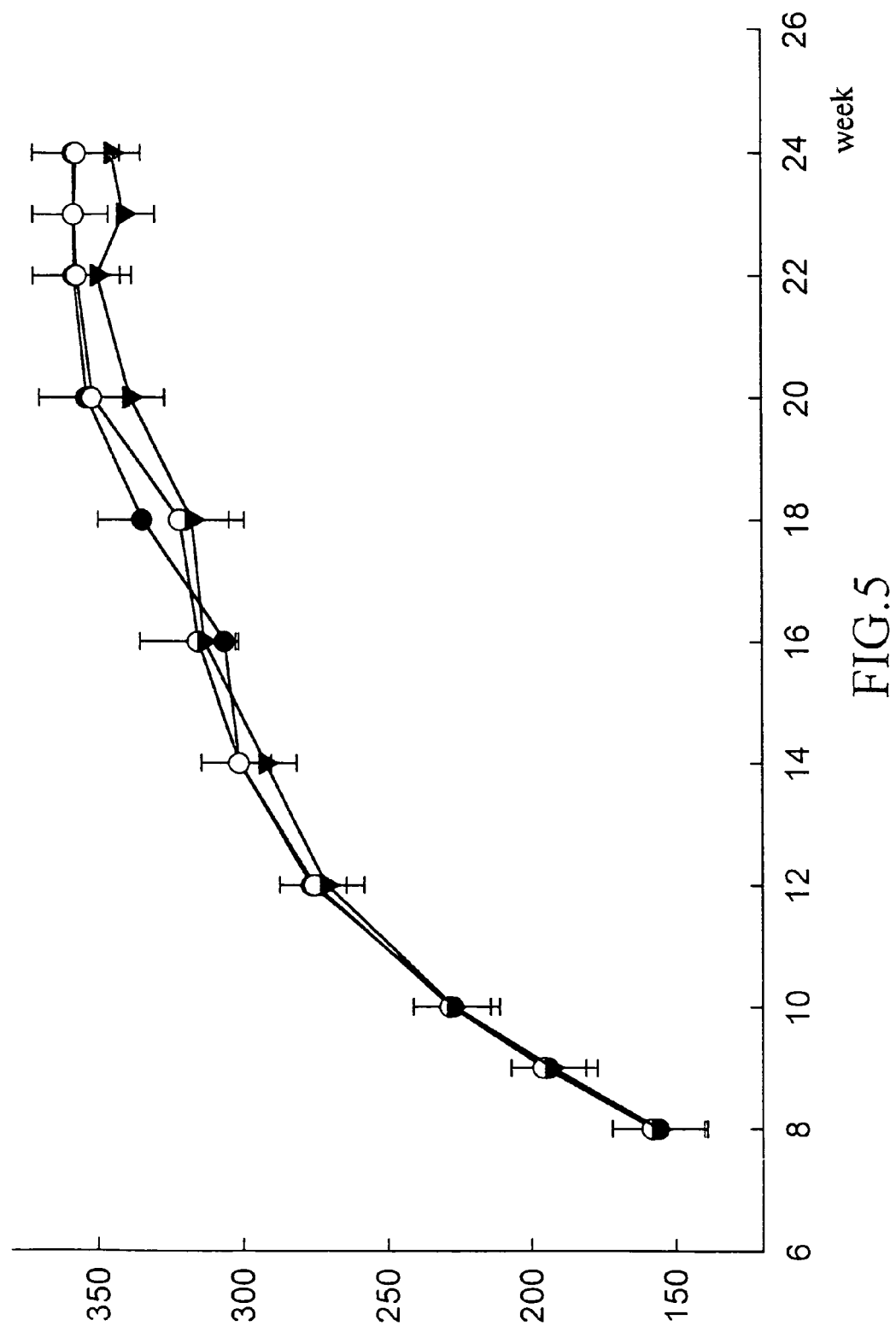

FIG. 5 shows the growth of the spontaneously hypertensive rats fed with the feeds containing ACEI.

Figure 6:
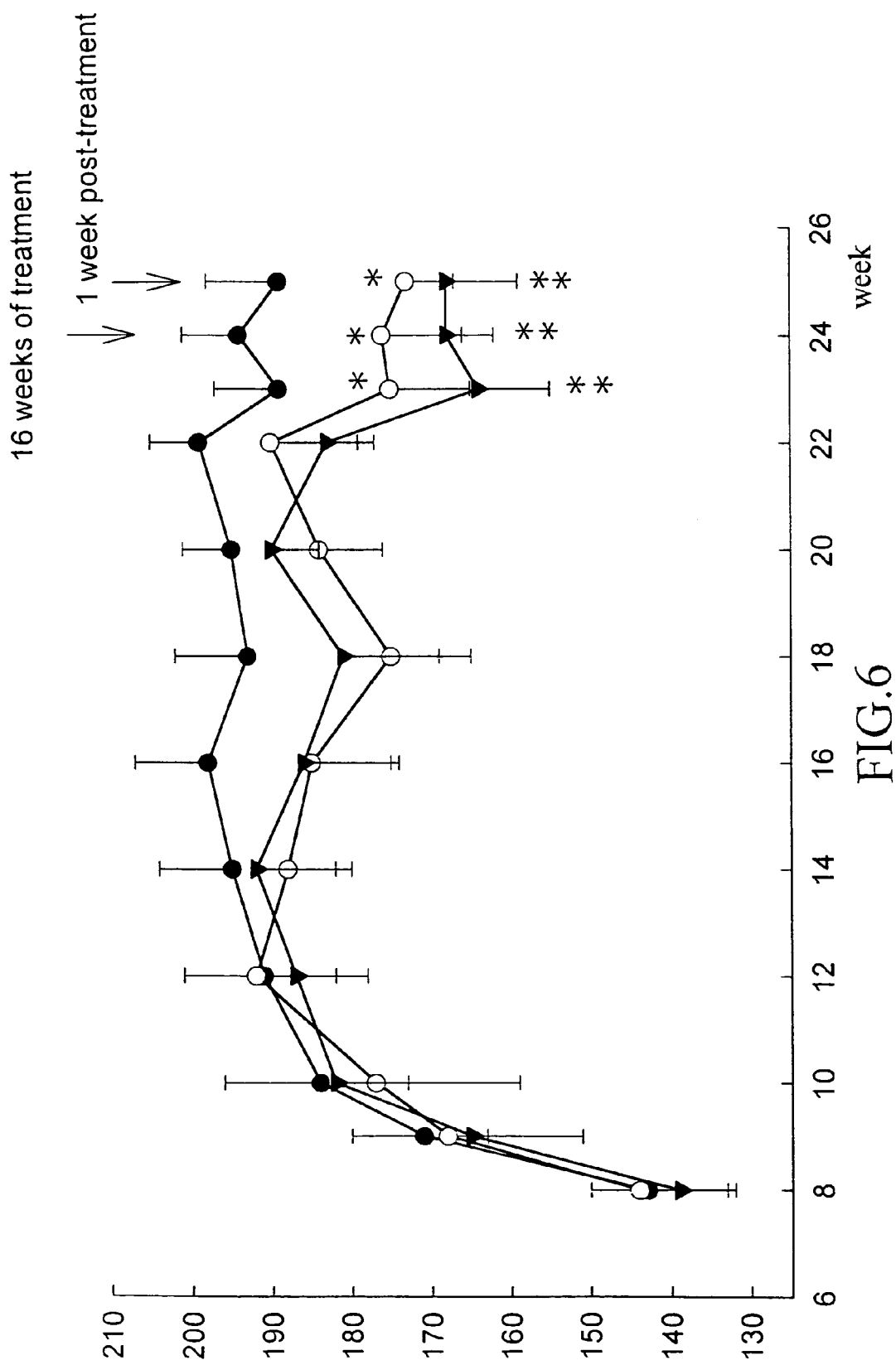

FIG. 6 shows the variation of blood pressure of the spontaneously hypertensive rats fed with the feeds containing ACEI.

DEAILED DESCRIPTION OF THE INVENTION

The peptides of the invention with ACE inhibitory activity have the following sequences:
Val-Leu-Pro (VLP);
Ile-Leu-Pro (ILP);
Val-Leu-Tyr (VLY);
Val-Leu-Pro-Pro (VLPP) (SEQ ID NO:1);
Ilu-Leu-Pro-Pro (ILPP) (SEQ ID NO:2).

These peptides can be isolated and purified from natural substances or prepared by known chemical synthesis method. According to the amino acid sequences, they can also be prepared by cloning the nucleotide sequences corresponding to the amino acid sequences of the peptides into suitable vectors and expressed in suitable host cells.

According to the invention, the wastes produced from the process of manufacturing chicken essence are used as the starting materials. They are incompletely hydrolyzed chicken meats and chicken bone residues. The materials are added into proper amount of water and protein hydrolase and hydrolyzed under proper reaction conditions. Then, the hydrolysate and the residues are separated and the liquid is collected. The liquid obtained is dried after further filtration and concentration to obtain the rough products. The products are purified to obtain the peptides. The amino acid sequences of the peptides are determined by sequence-determining machines. The peptides can be used as medicals, health foods or be added to foods.

The invention additionally discloses a process for the preparation of the products having ACE inhibitory activity, which comprises the following steps:

(a) adding protein hydrolase into the solution of chicken residues for reaction;

(b) separating the chicken residues and liquid after the reaction of step (a) and collecting the separated liquid; and (c) drying the liquid obtained from step (b) to obtain the products.

According to the invention, the process utilizes the wastes produced from the process for manufacturing chicken essence as the starting materials. The materials are incompletely hydrolyzed chicken meats and chicken bone residues. Those materials can be obtained from the factory of manufacturing chicken essence. The proper amount of water and protein hydrolase are added to the materials. The mixture is reacted under proper reaction conditions. The hydrolysate and the residues are separated and the liquid is collected. The liquid obtained is dried after further filtration and concentration in order to obtain the product. The product is detected to exhibit ACE inhibitory activity, which can be widely applied in health foods or used as food additives. If the hydrolyzed product is further purified, the peptides with ACE inhibitory activity can be obtained. The peptides can be used as pharmaceuticals.

The protein hydrolase in the step (a) can be any one having protein hydrolyzing activity, such as thermolysin, pepsin, trypsin bromelain, Alcalase, Flavorzyme or Esperase, preferably Alcalase.

The temperature and time of the hydrolysis reaction for the protein hydrolase depend on the species of the hydrolase selected. For instance, if Alcalase is used to proceed with the hydrolysis of the chicken residues, the preferred temperature is about 50 to 70° C., and the preferred reaction time is about 1 to 5 hours.

The hydrolysate after the hydrolysis is then separated into liquid and residues. Generally, the separation can be carried out by any operation steps of separation known to persons skilled in the art. The hydrolysate can be further concentrated to remove water so as to facilitate the drying process. For instance, the hydrolysate containing the residues can be put into filtration bag and centrifuged so as to collect the filtrates. The filtrates can be mixed with diatomite and subject to press-filtration and vacuum concentration.

The concentrated hydrolysate can be further subject to ultrafiltration to remove the molecules having higher molecular weights. The step utilizes the membranes with molecular weight cut-off of 100 to 20,000, preferably with molecular weight cut-off of 10,000, to proceed with the membrane filtration.

The drying step involved in the invention can be operated by any process known to persons skilled in the art, such as freeze drying, spray drying, drum-dryer drying and fluid-bed drying, preferably spray drying.

The products after drying can be applied in health foods or used as food additives. They can be further purified to obtain purified the peptides which can be used as pharmaceuticals. The purification step can be operated by any process known to persons skilled in the art, such as gel filtration, ion exchange chromatography and affinity chromatography.

According to one preferred embodiment of the invention, the products obtained are futher purified to obtain the peptides with ACE inhibitory activity. The amino acids sequences are determined as Val-Leu-Pro (VLP); Ile-Leu-Pro (ILP); Val-Ley-Tyr (VLY); Val-Leu-Pro-Pro (VLPP) (SEQ ID NO:1); and Ile-Lru-Pro-Pro (ILPP) (SEQ ID NO:2).

The peptides of the invention with ACE inhibitory activity can be prepared by known chemical synthesis. For example, the azide method, the acid chloride method, the acid anhydride method, the mixed acid anhydride method, the DCC method, the active ester method, the carboimidazol method, the oxidation-reduction method, the DCC-active method (see, for example, Schroder & Luhke, The Peptide, Vol. 1 (1996), Academic Press, New York, USA; or Izumiya et al., Peptide Synthesis, Maruzen Co., Ltd. (1975)). These peptide synthesis methods can be performed in either solid phase or liquid phase synthesis. The amino acids having a side chain functional group such as tyrosine and threonine are preferably protected in their side chain functional groups with known protective groups such as a benzyloxycarbonyl group, t-butoxycarbonyl group or benzyl group, etc. The protective groups can be removed by any known methods.

The following examples are for explication of the feasibility of the invention to substantiate the technical contents of the invention but not to limit the scope of the invention. Any variations and modifications to the invention for persons skilled in the art on the basis of the teaching of the prior art are within the scope of the invention.

EXAMPLE

Example 1

Preparation of the Peptides with ACE Inhibitory Activity from Hydrolyzed Chicken Residues Mixing 54 kg of chicken bone, 43.2 kg of water, 162 g of Neutrase, 270-g of Protamex, 162 g of polyphosphate and 32 g of tocopherol. The mixture is hydrolyzed at 62° C. for 2 hours. 7,480 g of bone residues is obtained after the hydrolysis. The hydrolysate is centrifuged to obtain 11,060 g of filtrate. 11,060 g of the filtrate is diluted with 4 volume of water (44,000 g) and re-hydrolyzed with 110 g of Alcalase at 65° C. for 2.5 hours. The hydrolysate is centrifuged to obtain filtrated residue 6,600 g. The filtrated liquid is added with 1 kg of diatomite and treated with press-filtration to obtain the re-hydrolysate with Brix 2.0. To facilitate the spray drying, the re-hydrolysate is concentrated and ultrafiltrated with the membrane of molecular weight cut-off of 10,000. The present example concentrates the mixture to Brix 11.8 and then to proceed with spray drying. The hydrolysate for the spray drying is 4,850 g. After spray drying, the powder 391.4 g is obtained.

Example 2

Methods for Determination of ACE Inhibitory Activity

1. Re-hydrolysis of the Chicken Bone Hydrolysate

The chicken filtrate obtained from Example 1 is diluted with 2 volume of water and mixed and divided into five groups. 1% of Bromelain, Alcalase, Flavorzyme, Esperase and water based on the weight of hydrolysate are added to every group. These mixtures are reacted at 60° C. for 2.5 hours and then heated to 90° C. for 10 minutes to inactivate the enzymes. The hydrolysate is centrifuged at 10,000 g for 20 minutes. The upper solution is collected for the determination of ACE inhibitory activity. The results are shown in Table 1. The $IC_{50}$ value is the concentration of ACEI required for the inhibition of 50% ACE activity.

2. Determination of ACEI Activity (a) HHL method

This method is modified from the method of Cushman and Cheung, 1971, Biochem. Pharmacol., 20:1637. 80 µl of hydrolysate is added to HHL incubation solution. The incubation solution contains 5 mM of HHL (Hippuryl-Histidyl-Leucine) and 0.3 M of sodium chloride in 0.1 M of sodium borate buffer. The solution is incubated at 37° C. (pre-heated) for 5 minutes. 20 µl of 0.1 U/ml ACE solution is added to the solution and incubated at 37° C. for 30 minutes. 1N of hydrochloric acid is added to the solution. The solution is then extracted with 1.7 ml of ethyl acetate. The organic part is then subject to vacuum drying. The dried powder is resolved in 1 ml of water. The absorption value is determined at UV 228 nm.

The protein concentration of the chicken re-hydrolysate is determined by Micro-biuret method which is known in the art. The re-hydrolysate solution is separately diluted to 50, 100, 200, 300 and 400 volumes of such five concentrations. The regression curve is plotted as a log function, and the $IC_{50}$ value is determined from the log function.

(b) Sigma kit method

This method is modified from the manual of Sigma kit. 0.05 ml of deion water (for the control) or 0.05 ml samples (for the test) are added to 1 ml reaction solution (ACE substrate). 0.05 ml of calibration solution (porcine ACE) is added to the solution. The solution stands at 37° C. for 5 minutes. The absorption value at 340 nm is determined (this value is as referred to the staring A value). After the measure, the mixture is reset to the water bath. After 5 minutes, the absorption value is determined again (the value is as referred to final A value). These values obtained are calculated as follows:

$$\text{ACE inhibitory activity} = \frac{\text{Starting A value (samples)} - \text{Final A value}}{\text{Starting A value (calibration solution)} - \text{Final A value}} \times \text{The activity of the calibration solution (generally 45 U/L)}$$

TABLE 1

$IC_{50}$ values of different re-hydrolysate

| | $IC_{50}$ value determined by HHL method (mg/ml) | $IC_{50}$ value determined by Sigma kit method (mg/ml) |
|---|---|---|
| Alcalase Re-hydrolysate | 0.0953 | 0.2725 |
| Bromelain Re-hydrolysate | 0.1525 | 0.3134 |
| Esperase Re-hydrolysate | 0.1993 | 0.3724 |
| Flavorzyme Re-hydrolysate | 0.3121 | 0.463 |
| Control | 0.6292 | 1.424 |

From the results shown in Table 1, it is understood that whether the $IC_{50}$ value for ACE inhibitory activity is determined by HHL method or Sigma kit method, the order of the activity of the re-hydrolysate is identical. The re-hydrolysate product prepared by Alcalase has the most significant activity.

Example 3

Method of Ultrafiltration

To further purify the re-hydrolysate and facilitate the preparation of products by spray drying, ultrafiltration is performed to concentrate the product. The ultrafiltration membranes selected are those with molecular weight cut-off of 10,000 and 500, respectively. The re-hydrolysate is filtrated with the membranes with molecular weight cut-off of 10,000 and 500 in order. The ACE inhibitory activity of the dialysates is determined by the above-mentioned methods. The results are shown in Table 2:

TABLE 2

| | |
|---|---|
| Original re-hydrolysate | $IC_{50}$ = 0.33184 mg/ml |
| The part not passing the membrane with molecular weight cut-off of 10,000 | $IC_{50}$ = 0.34725 mg/ml |
| The part passing the membrane with molecular weight cut-off of 10,000 | $IC_{50}$ = 0.23825 mg/ml |
| The part passing the membrane with molecular weight cut-off of 10,000 but not passing the membrane with molecular weight cut-off of 500 | $IC_{50}$ = 0.37065 mg/ml |
| The part passing the membrane with molecular weight cut-off of 10,000 and passing the membrane with molecular weight cut-off of 500 | $IC_{50}$ = 0.37724 mg/ml |

From the above table, it is understood that the membrane with molecular weight cut-off of 10,000 may remove a part of the substances with higher molecular weights (i.e., those with shorter retention time). The significant difference between the substances before and after ultrafiltration with the membrane with molecular weight cut-off of 500 is observed. The purer substances with lower molecular weight can be obtained. In comparison with the $IC_{50}$ values shown in Table 2, it is found that the substances passing the membrane with molecular weight cut-off of 10,000 have more significant ACE inhibitory activity. As for the membrane with molecular weight cut-off of 500, the activity of the substances before and after ultrafiltration is not significantly different. Therefore, the treatment of the re-hydrolysate with the membrane with molecular weight cut-off of 10,000 may remove a part of the substances of higher molecular weights and the precipitate of the re-hydrolysate, and effectively increase the $IC_{50}$ values of the re-hydrolysates.

Example 4

Purification of the Peptides 1 g of the previous spray-dried powder is dissolved in 50 ml of water. The solution is filtrated with 0.45µ, centrifugation tubes and purified and characterized by the following steps.

Figure 1:
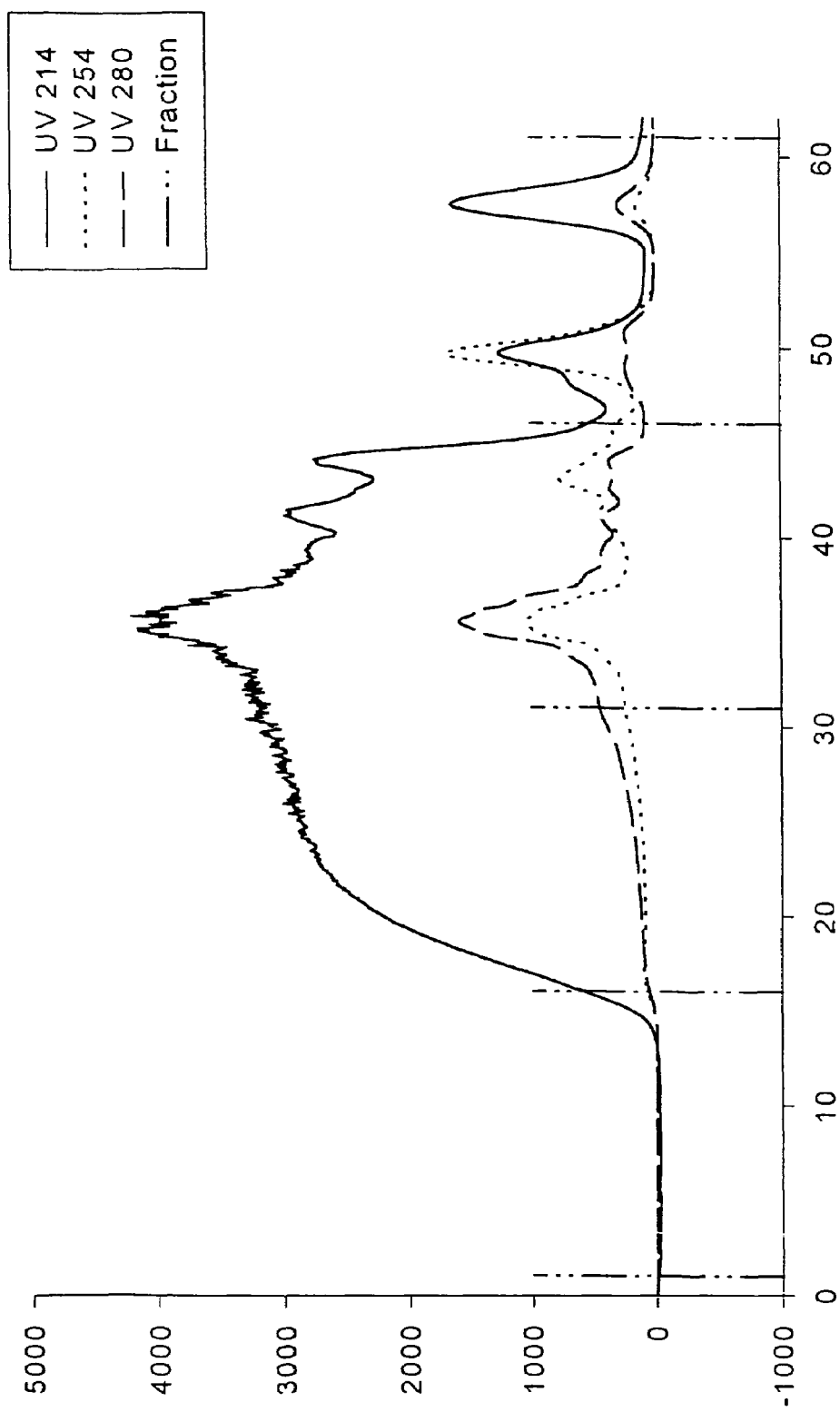
FIG. 1 shows the result of isolation of the peptides prepared according to the invention at the first stage by use of a size exclusion column.

1. The size exclusion column is utilized at the first separation stage. The condition is as follows:
   System: AKTA purifier
   Separation column: Superdex Peptide HR 1030
   Mobile phase: 0.5 µl
   Elution solution: 5% alcohol dissolved in water
   Flow rate: 0.5 ml/min
   Detector: Detection with 214, 254 and 280 nm
   The results are shown in FIG. 1.

The above fractions are repeatedly collected for ten times. The collected solution is freeze-dried with Speed Vac. The total dry weights of Fractions 2, 3 and 4 are 0.054, 0.143 and 0.019 mg, respectively. The three fractions are re-dissolved in water for twice and formulated to two concentrations, 1 mg/ml and 10 mg/ml. The 1 mg/ml solution is used for the determination of ACE inhibitory activity. The 10 mg/ml solution is used for purification. Fractions 2, 3 and 4 (1 mg/ml) are determined by Sigma kit as having 0%, 46.69% and 27.71% ACE inhibitory activity. Fraction 3 (hereinafter as referred to A3) is proceeded with the following purification.

2. RP18 column is utilized at the second stage. The conditions are as follows:
   System: AKTA purifier
   Separation column: LiChrosorb RP-18 (7 µm) pre-packed column RT250-25
   Mobile phase: 5000 µl
   Elution solution A1: Water containing 0.1% TFA
   Elution solution B1: Methanol containing 0.1% TFA
   Gradient: 0% of B1 utilized in 0.5 volume of column
   0-100% of B1 utilized in 3 volume of column
   100% of B 1 utilized in 1.2 volume of column
   Flow rate: 0.5 ml/min
   Detector: Detection with 214, 254 and 280 nm
   The results are shown in FIG. 2.

Figure 2:
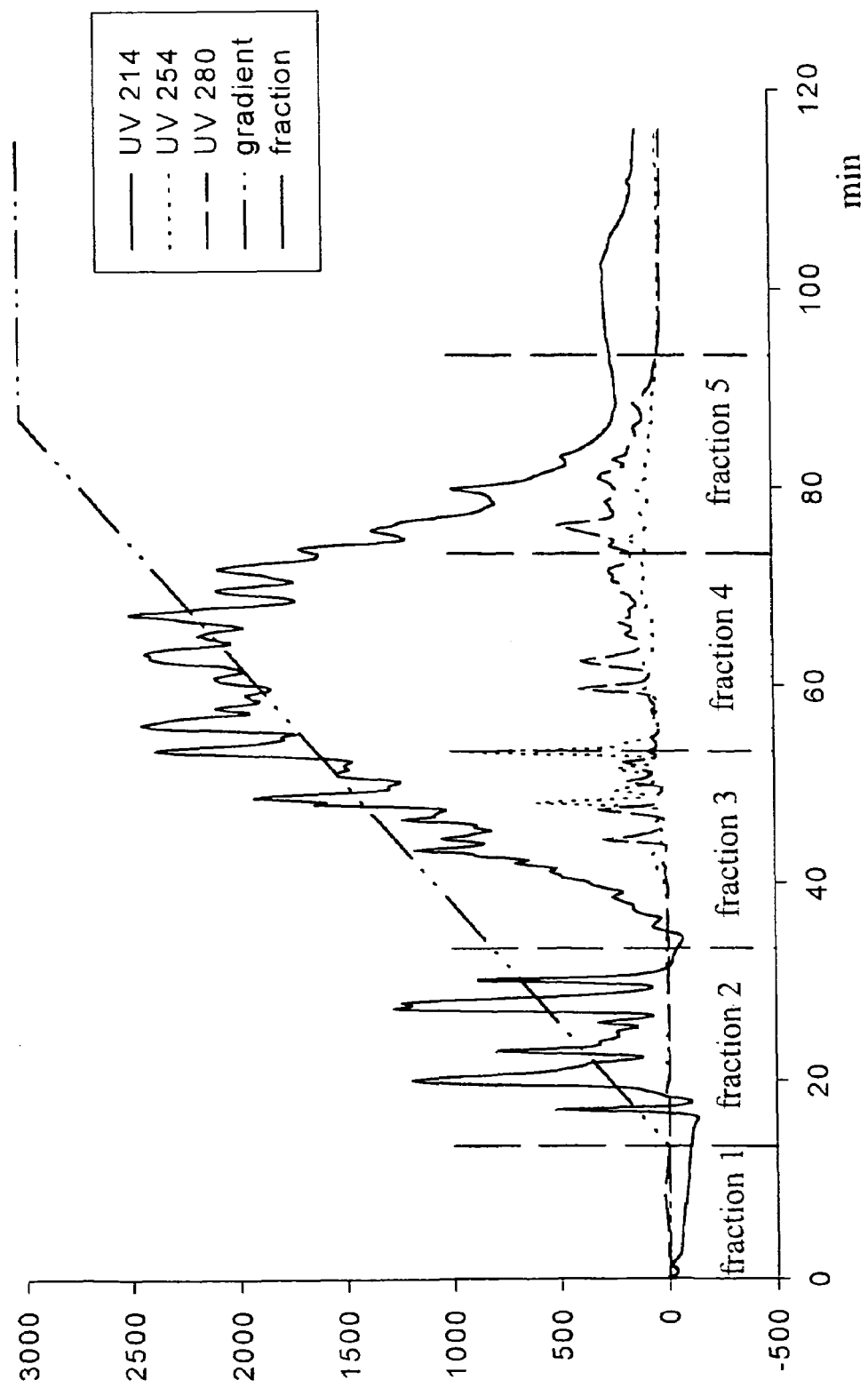
FIG. 2 shows the result of purification of the peptides prepared according to the invention at the second stage by use of a RP 18 column.

The results of FIG. 2 can be separated into five fractions. The five fractions are collected for three times and dried with Speed Vac. The weights of the dried solid substances are 0.0085, 0.0222, 0.0303, 0.0432 and 0.0214, respectively. As the sane as the previous operation, the five fractions are formulated to 1 mg/ml solution used for the determination of ACE inhibitory activity. The 10 mg/ml solution is used for purification. The inhibition of ACE of the five fractions is determined by Sigma kit. The results are as follows:

TABLE 3

| Fraction | Inhibition of ACE (%) |
| --- | --- |
| Fraction 1 (A3-B1) | 0 |
| Fraction 2(A3-B2) | 0 |
| Fraction 3(A3-B3) | 4.76 |

TABLE 3-continued

| Fraction | Inhibition of ACE (%) |
| --- | --- |
| Fraction 4(A3-B4) | 59.37 |
| Fraction 5(A3-B5) | 36.51 |

From Table 3, it is understood that Fraction A3-B4 has the most significant ACE inhibitory activity. Therefore, Fraction A3-B4 is further purified.

3. Analytical class of RP18 column is utilized at the third stage. The conditions are as follows:
   System: AKTA purifier
   Separation column: Sephasil Peptide RP-18 (5 µl) ST 4.6/250
   Mobile phase: 100 µl
   Elution solution A1: Water containing 0.1% TFA
   Elution solution B1: Methanol containing 0.1% TFA
   Gradient: 0% of B1 utilized in 2 volume of column
   0-100% of B1 utilized in 10 volume of column
   100% of B1 utilized in 3 volume of column
   Flow rate: 0.6 ml/min
   Detector: Detection with 214, 254 and 280 nm
   The results are shown in FIG. 3.

Figure 3:
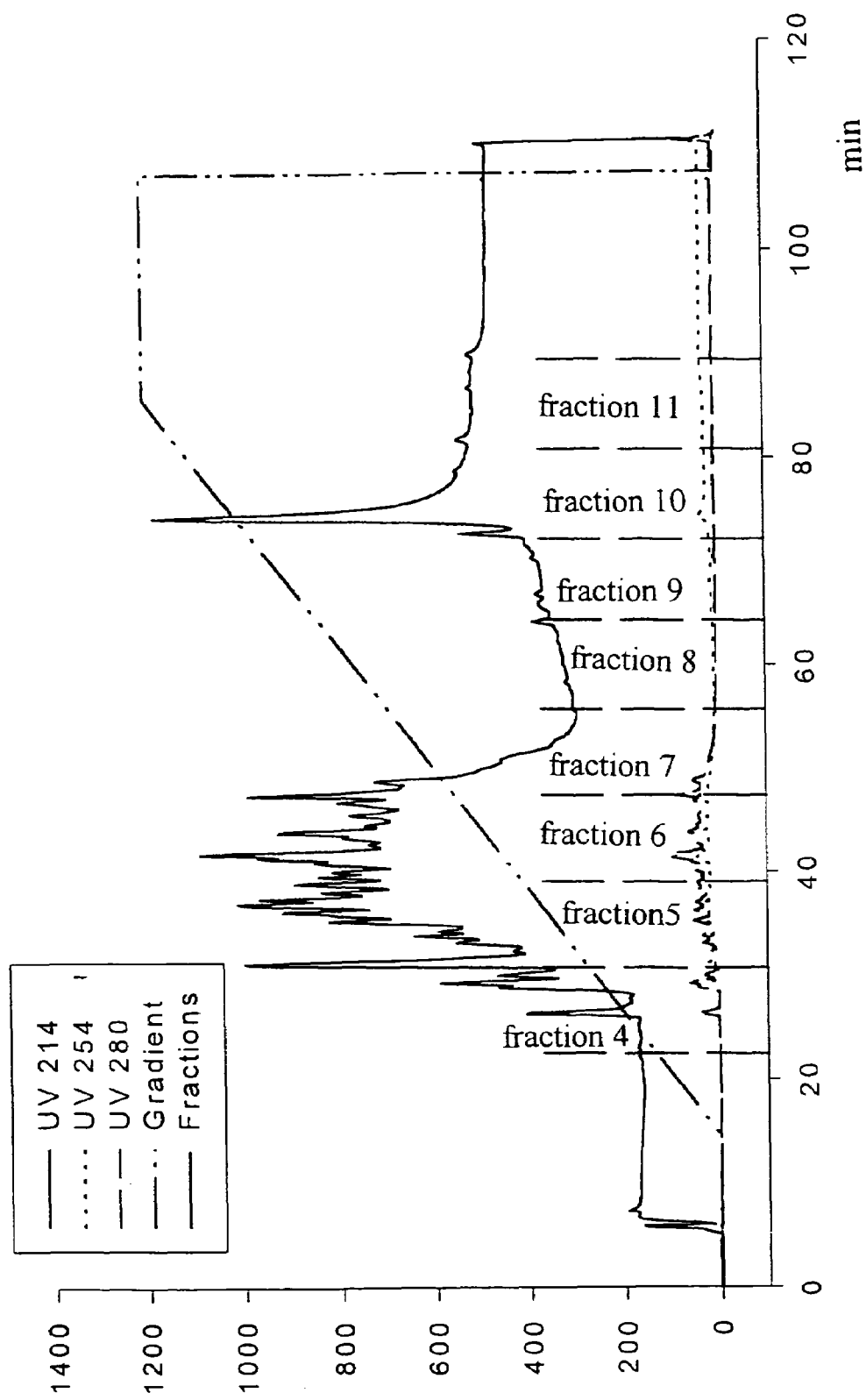
FIG. 3 shows the result of purification of the peptides prepared according to the invention at the third stage by use of an analytical class C-18 column.

The results of FIG. 3 can be divided into eight fractions. The eight fractions are collected for fifteen times and vacuum dried with Speed Vac. The eight fractions are formulated to 1 mg/ml solution for the determination of ACE inhibitory activity. The 10 mg/ml solution is used for the purification. The inhibition of ACE of the eight fractions are shown as follows:

TABLE 4

| Fraction | Inhibition of ACE (%) |
| --- | --- |
| Fraction 4(A3-B1-C4) | 0 |
| Fraction 5(A3-B2-C5) | 21.92 |
| Fraction 6(A3-B3-C6) | 32.19 |
| Fraction 7(A3-B4-C7) | 0 |
| Fraction 8(A3-B5-C8) | 0 |
| Fraction 9(A3-B5-C9) | 0 |
| Fraction 10(A3-B5-C10) | 0 |
| Fraction 11(A3-B5-C11) | 13.70 |

Table 4 reveals that Fraction A3-B4-C6 has the most significant ACE inhibitory activity. Therefore, Fraction A3-B4-C6 is further purified.

4. Analytical class of C-18 column is utilized at the fourth stage. The conditions are as follows:
   System: AKTA purifier
   Separation column: Sephasil Peptide RP-18 (5 µl) ST 4.6/250
   Mobile phase: 100 µl
   Elution solution A1: Water containing 0.1% TFA
   Elution solution B1: Ethylnitrile containing 0.1% TFA
   Gradient: 10% of B1 utilized in 1 volume of column
   10-30% of B1 utilized in 5 volume of column
   30-60% of B1 utilized in 4 volume of column
   60-100% of B1 utilized in 2 volume of column
   100% of B1 utilized in 1 volume of column
   Flow rate: 1 ml/min
   Detector: Detection with 214, 254 and 280 nm
   The results are shown in FIG. 3.

The five more apparent peaks in FIG. 4 are designated as A3-B4-C6-D1 to D5. The sequences of them are determined by sequence-determining machine. Five short-chain peptides, Val-Leu-Pro (VLP), Ilu-Leu-Pro (ILP), Val-Leu-Tyr (VLY), Val-Leu-Pro-Pro (VLPP) and Ilu-Leu-Pro-Pro (ILPP) are obtained. The ACE inhibitory activity of them ($IC_{50}$) is determined. The results are shown in Table 5:

TABLE 5

The ACE inhibitory activity of the peptides isolated and purified from the invention

| Sequence of peptides | $IC_{50}$ (μM) |
|---|---|
| VLP | 81 |
| VLY | 31 |
| VLPP | 97 |
| (SEQ ID NO:1) | |
| ILPP | 172 |
| (SEQ ID NO:2) | |
| ILP | 32 |

Example 5

Animal Test

Twenty male SHR/N (spontaneously hypertensive rats; Okamoto-Aoki SH/N) rats aged 7 weeks were purchased. The rats were fed with powder feeds in stainless cages. The rats aged 8 weeks were randomly divided into three groups, and 6-7 rats (about 157 g of body weight) of a group. The three groups were fed with normal feed (control), 1% ACEI and 3% ACEI. These rats were freely accessible to food and water. The cages was kept at a temperature of 24±1° C., relative humidity of 50-70%. The period of the test is 17 weeks. During the period of the test, the body weight and blood pressure were recorded every one to two weeks.

The systolic blood pressure and heart rate of the rats were measured by programmed electrophygomanometer (PB98A, Softron). The results are shown in FIGS. 5 and 6.

FIG. 5 shows the growth of the spontaneously hypertensive rats by feeding the feeds containing ACEI. The body weight of the rats of the three groups increases along with the time increased. There are not significant differences among the three groups. The amount of the feed is not significant different (the digested amount of the feed for control, 1% ACEI and 3% ACEI groups is 20.1±1.5, 20.3±1.7, 19.6±1.3 g, respectively). The result demonstrates that the addition of ACEI powder influences neither the appetite nor the growth.

FIG. 6 shows the variation of blood pressure of the spontaneously hypertensive rats by feeding the feeds containing ACEI. As a whole, the blood pressure of the spontaneously hypertensive rats gradually increase with the age. If the rats are not fed with ACEI, the blood pressure may maintain at a stable value as it increase to about 200 mm Hg. The blood pressure of the rats fed with ACEI for 8 weeks (aged 16 weeks) is slightly controlled, but is not different from that of the control. After 15 weeks, the blood pressure of the rats fed with ACEI is significantly lower than that of the control ($p<0.05$). The blood pressure of the rats fed with 1% and 3% ACEI reduces 14 and 25 mm Hg, respectively. The tendency lasts until the rats are aged 24 weeks. This demonstrates that the long period digestion of the re-hydrosate indeed exhibits the physiological efficacy on reduction of blood pressure. The more dose, the more significant efficacy on reduction of blood pressure. As termination of feeding the rats with ACEI for one week, the efficacy on reduction of blood pressure may still last for a period.

The invention claimed is:

1. A process for the preparation of peptides having angiotensin converting enzyme inhibitory activity, which comprises the following steps:
   (a) adding NEUTRASE, a protein hydrolasea, to chicken bones in a liquid to hydrolyze the chicken bones at 62° C. for 2 hours;
   (b) re-hydrolyzing the hydrolyzate of step (a) with ALCALASE a protein hydrolase, at 65° C. for 2.5 hours;
   (c) separating the resulting hydrolyzed chicken bones residues and liquid after step (b) by a process selected from the group consisting of press filtration and ultrafiltration employing a membrane with a molecular weight cut off of 10,000, and then concentrating the separated liquid by drying; and
   (d) purifying peptides having angiotensin converting enzyme inhibitory activity from the dried product obtained from step (c), wherein the peptides have the sequence selected from the group consisting of VLY, VLPP (SEQ ID NO: 1), and ILPP (SEQ ID NO: 2).

* * * * *

SEQUENCE LISTING

```
<160> NUMBER OF SEQ ID NOS: 4

<210> SEQ ID NO 1
<211> LENGTH: 4
<212> TYPE: PRT
<213> ORGANISM: Artificial Sequence
<220> FEATURE:
<223> OTHER INFORMATION: synthetic peptide

<400> SEQUENCE: 1

Val Leu Pro Pro
1

<210> SEQ ID NO 2
<211> LENGTH: 4
<212> TYPE: PRT
<213> ORGANISM: Artificial sequence
<220> FEATURE:
<223> OTHER INFORMATION: synthetic peptide

<400> SEQUENCE: 2

Ile Leu Pro Pro
1

<210> SEQ ID NO 3
<211> LENGTH: 4
<212> TYPE: PRT
<213> ORGANISM: Artificial Sequence
```

```
<220> FEATURE:
<223> OTHER INFORMATION: synthetic peptide

<400> SEQUENCE: 3

Tyr Ser Trp Ala
1

<210> SEQ ID NO 4
<211> LENGTH: 5
<212> TYPE: PRT
<213> ORGANISM: Artificial Sequence
<220> FEATURE:
<223> OTHER INFORMATION: synthetic peptide

<400> SEQUENCE: 4

Gln Lys Pro Lys Arg
1               5
```